United States Patent [19]

Kausek

[11] Patent Number: 4,966,133
[45] Date of Patent: Oct. 30, 1990

[54] KNEE BRACE FOR CONTROL OF LIGAMENT STABILITY

[76] Inventor: James H. Kausek, 31 Stanwood Rd., Swampscott, Mass. 01907

[21] Appl. No.: 241,588

[22] Filed: Sep. 8, 1988

[51] Int. Cl.$^5$ .............................................. A61F 5/00
[52] U.S. Cl. .................................... 128/80 C; 128/165
[58] Field of Search ...................... 128/80 C, 80 F, 88, 128/165

[56] References Cited

U.S. PATENT DOCUMENTS

| | | | |
|---|---|---|---|
| 3,387,305 | 6/1968 | Shafer | 128/80 C |
| 3,581,741 | 6/1971 | Rosman | 128/80 C |
| 4,144,592 | 3/1979 | Larson | 128/80 C |
| 4,372,298 | 2/1983 | Lerman | 128/88 |
| 4,493,316 | 1/1985 | Reed | 128/80 C |
| 4,506,661 | 3/1985 | Foster | 128/88 |
| 4,554,913 | 11/1985 | Womack | 128/80 C |
| 4,556,053 | 12/1985 | Irons | 128/80 C |
| 4,624,247 | 11/1986 | Ford | 128/80 F |
| 4,632,098 | 12/1986 | Grunder | 128/80 C |
| 4,681,097 | 7/1987 | Pansiera | 128/80 C |
| 4,732,143 | 3/1988 | Kausek | 128/80 F |
| 4,733,656 | 3/1988 | Marquette | 128/80 F |
| 4,791,916 | 12/1988 | Paez | 128/80 C |
| 4,802,466 | 2/1989 | Meyers | 128/80 C |

OTHER PUBLICATIONS

McDavid Knee Guard Preventive Knee Brace-M1 Series, McDavid Knee Guard, Inc., Clarendon Hills, Ill.
McDavid M-155 Knee Guard, McDavid Knee Guard, Inc., Clarendon Hills, Ill.
Anderson Knee Stabler Protective Knee Brace, Omni Scientific, Inc., Martinez, Calif.
Polyaction Protective Knee Orthosis, Freeman, Sturgis, Mich.
Generation Orthotics, Inc. trade brochures entitled: "What Makes A Winner?" and The Knee Brace That Climbed Mount Everest, describing the Generation II Poli-Axial Knee Brace.

*Primary Examiner*—Edgar S. Burr
*Assistant Examiner*—Huong Q. Pham
*Attorney, Agent, or Firm*—Wolf, Greenfield & Sacks

[57] ABSTRACT

A knee brace for control of ligament instability in all planes having upper and lower cuffs above and below the knee, a polycentric hinge on the lateral side of the knee, and a medial articulation plate on the medial side of the knee. The cuffs are attached to the leg with non-stretchable straps and provide anterior-posterior stability. The medial pivot plate is designed to stabilize the brace on the medial side of the knee and in conjunction with the lateral hinge and a lateral plate provides medial-lateral stability.

26 Claims, 11 Drawing Sheets

KNEE BRACE FOR CONTROL OF LIGAMENT STABILITY

BACKGROUND OF THE INVENTION

This invention concerns a knee brace for controlling ligament instability, and more particularly to a knee brace having upper and lower cuffs joined by a polycentric hinge on the lateral side of the brace and a pivotal articulation plate at the medial side of the brace.

When the ligaments surrounding the knee have been traumatized by injury or by surgery, a supporting brace is used to provide stability while still allowing movement of the knee. The brace should provide stability when forces are applied to the knee in the medial and lateral (side) planes and in the anterior (front) and posterior (rear) planes. In addition, the brace should provide rotational stability so as to prevent excessive axial rotation of the tibia with respect to the femur. The brace should also prevent forward movement of the tibia with respect to the femur, a function provided in the normal knee by the anterior cruciate ligament.

A knee brace for control of ligament instability is described in U.S. Pat. No. 4,633,867 to Kausek et al. That brace includes a thigh cuff, a shin plate, and a rear calf cuff. In that brace two polycentric hinges are provided at the medial and lateral sides of the brace. While use of polycentric hinges on both sides of the knee provides good ligament control. The movement of the knee is somewhat restricted.

Knee braces having a lateral hinge, but no medial hinge, are often worn by football players to prevent injury. They may also be used for rehabilitation or to support a knee which exhibits chronic instability. The lateral hinge, which may be monocentric or polycentric, has upper and lower lateral plates which are either taped to the leg or inserted in a wrap-around neoprene sleeve by Velcro straps with closures. This brace provides greater support when taped to the leg, but taping is uncomfortable and not practical for daily use. The brace provides less support when attached via the neoprene sleeve.

It would thus be desirable to provide a knee brace which provides good ligament control while allowing a natural range of movement of the knee, and which is comfortable to wear and easily removable for daily use It is also desirable to provide a brace which offers some adjustability as to size and thus can be sold as an of-the-shelf item. These and other features are provided by the knee brace of the present invention.

SUMMARY OF THE INVENTION

The knee brace of this invention includes upper and lower cuffs positioned above and below the knee which are attached to the leg by substantially non-stretchable cuff straps. A lateral hinge having upper and lower hinge arms and at least one pivot point is positioned at the lateral side of the knee, with the upper hinge arm connected to a lateral portion of the upper cuff and the lower hinge arm connected to a lateral portion of the lower cuff. A medial articulation plate is positioned at the medial side of the knee which has an inner surface for engaging the medial knee joint. The medial plate is pivotally connected to the upper cuff and connected by straps to the lower cuff. The upper and lower cuffs and the non-stretchable cuff straps provide anterior-posterior stability to the knee joint while the lateral hinge and medial plate provide medial-lateral stability.

The upper and lower cuffs each comprise a hard outer shell for rigidity and strength with a softer, non-abrasive lining for comfort. Each cuff is shaped to engage three sides of the leg and is releasably attached thereto by non-stretchable straps with adjustable fasteners. The hard molded shell provides a rigid framework in the vertical direction for secure attachment and positioning of the upper and lower arms of the polycentric hinge on the lateral side of the brace. Preferably, a lateral plate is provided for engaging the lateral side of the knee, which plate may be attached either to the hinge or to a cover on the hinge.

In order to provide some adjustability as to size, the hard and substantially rigid molded shells of the upper and lower cuffs have some medial-lateral flexibility to accommodate legs of varying girth. The soft foam liner of the cuffs also accommodates differences in leg girth. A series of vertically aligned apertures are provided on the lateral portions of the upper and lower cuffs for selected attachment of the hinge arms to further provide adjustability as to size.

DETAILED DESCRIPTION OF THE PREFERRED EMBODIMENTS

A first preferred embodiment of the knee brace of this invention is shown in FIGS. 1-7. The brace shown is designed for use on the left knee; a symmetrical version may be provided for use on the right knee.

Figure 1:
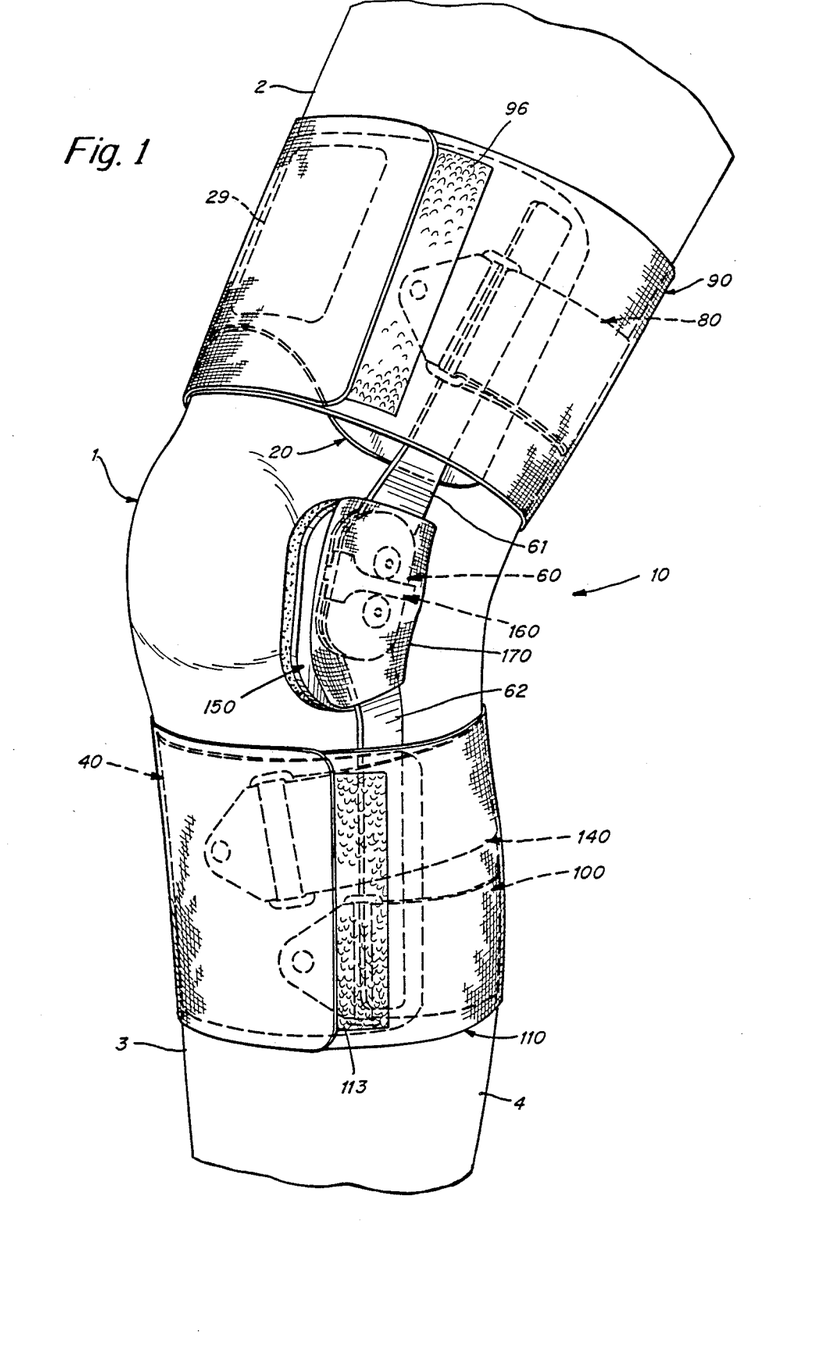
FIG. 1 is a lateral perspective view of a left knee and the knee brace of this invention.
Figure 2:
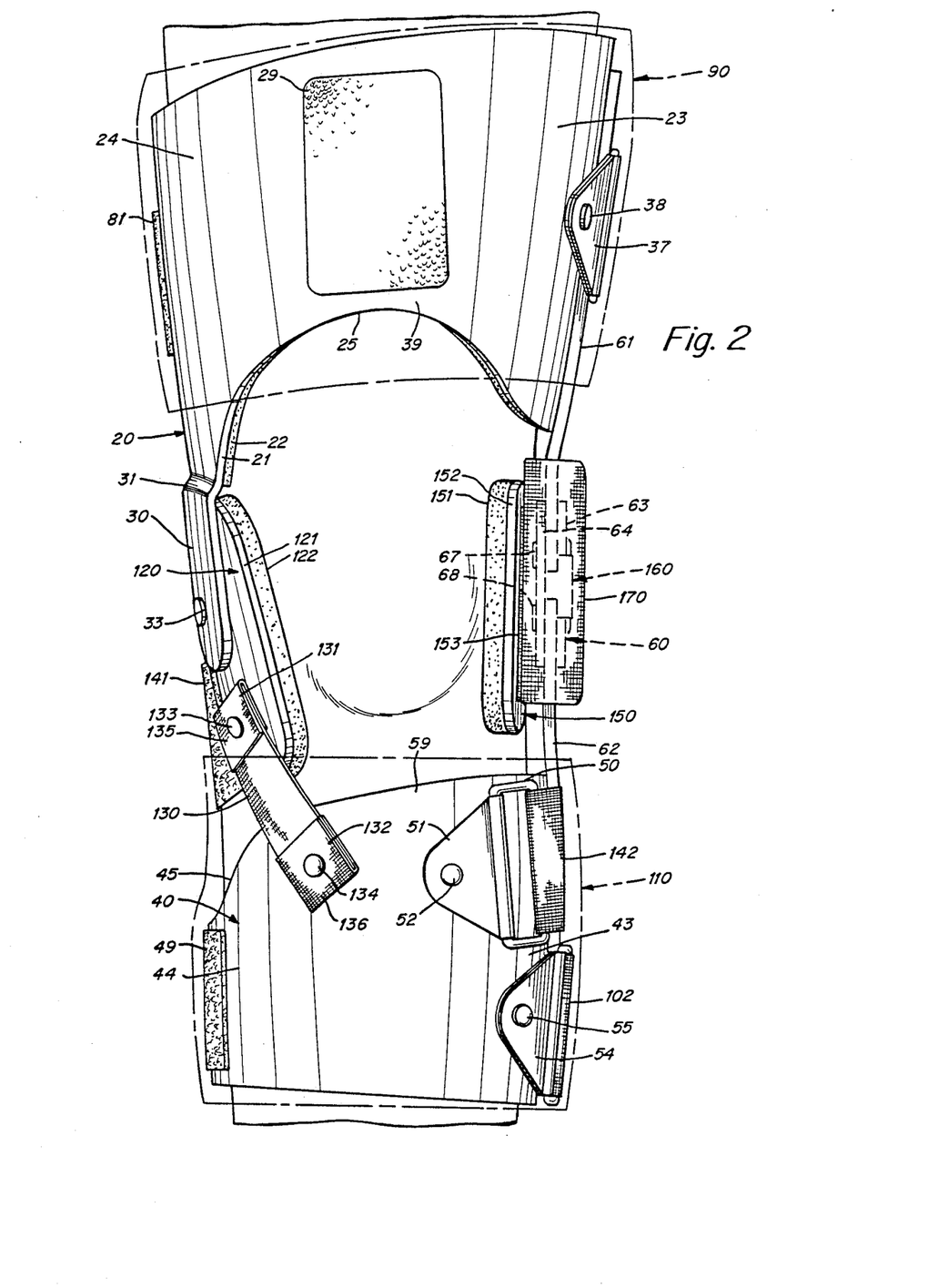
FIG. 2 is a front elevation view of the left knee and brace of FIG. 1 with the outer thigh and calf bands shown in phantom lines.
Figure 3:
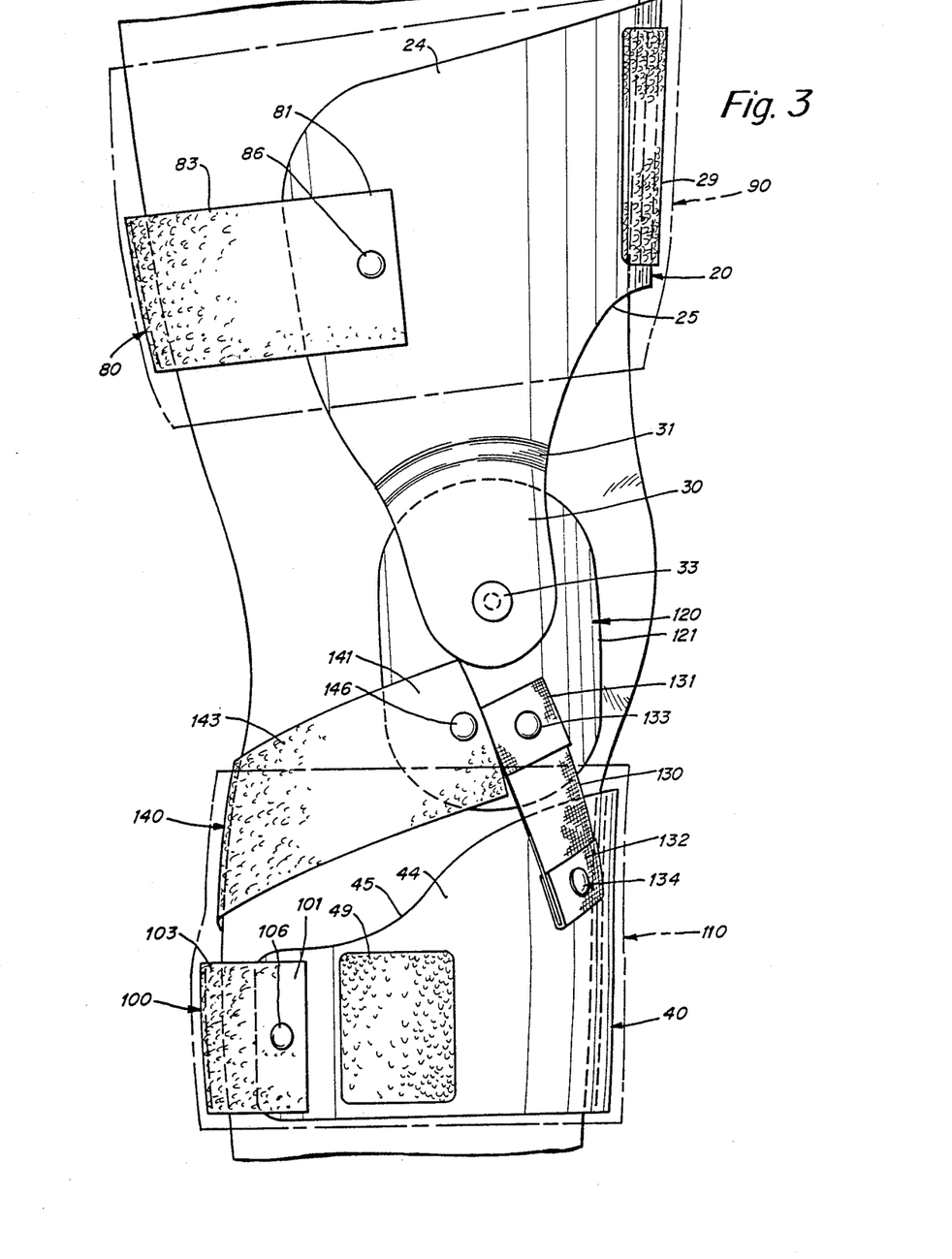
FIG. 3 is a medial elevation view of the left knee and brace of FIG. 1 with the outer thigh and calf bands shown in phantom lines.

As shown in FIGS. 1-3, the brace includes an upper thigh cuff 20 secured to the leg above the knee by a non-stretchable upper cuff strap 80, and a lower shin cuff 40 secured to the leg below the knee by a non-stretchable lower cuff strap 100. On the lateral side of the brace, a polycentric hinge 60 is positioned at the lateral side of the knee with hinge arms or shafts 61, 62 connected to the thigh and shin cuffs, respectively. On the medial side of the brace, a medial plate 120 is positioned at the medial side of the knee which has an upper pivotal connection 33 to a lower flange 30 on thigh cuff 20 and two lower nonpivotal connections to the shin cuff 40 via a stretchable anterior strap 130 and a nonstretchable posterior strap 140. In addition, a pair of wide, stretchable, upper and lower outer bands 90, 110, respectively, are wrapped around the exterior of the brace at the thigh and calf.

Figure 5:
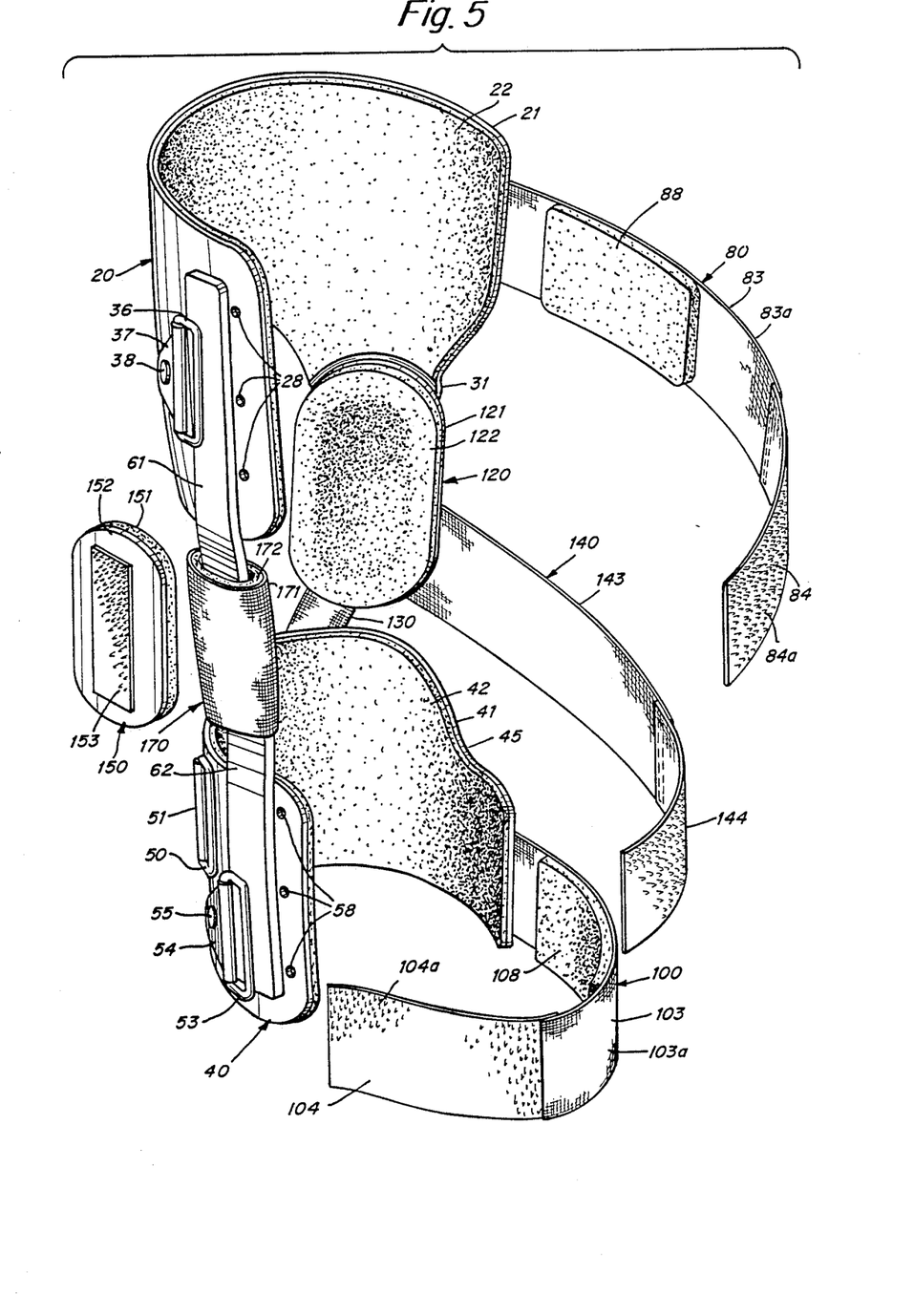
FIG. 5 is an exploded rear perspective view of the brace of FIG. 1 (without the outer thigh and calf bands).

An exploded perspective view of the various brace components, from the rear, is shown in FIG. 5.

As shown in FIGS. 1-3, the knee brace 10 is positionable on the thigh 2, shin 3 and calf 4 of the wearer for providing control of ligament instability to knee joint 1. Thigh cuff 20 has a hard outer shell 21 and a soft padded lining 22. Thigh cuff 20 is shaped to conform to the wearer's thigh and has an anterior portion 39 engaging the front (anterior) of the thigh and lateral and medial portions 23, 24 covering the lateral and medial sides of the thigh, respectively. The lower anterior edge 25 of the thigh cuff is curved upwardly to reduce the weight of the cuff and to prevent interference with the upper portion of the knee joint.

A non-stretchable upper cuff strap 80 extends behind the leg above the knee and releasably secures thigh cuff 20 to the leg via an adjustable fastener at one end. Upper cuff strap 80 includes a medial portion 83 having Velcro loops 83a on its outer surface and padding 88 on its inner surface and a lateral portion 84 having Velcro hooks 84a on its outer surface (FIG. 5). Medial end 81 of upper cuff strap 80 is permanently attached to medial portion 24 of thigh cuff 20 by rivet 86 (FIG. 3). Lateral end 82 of thigh strap 80 is adjustably and releasably attached to lateral portion 23 of thigh plate 20 (see FIG. 4) by passing lateral portion 84 through ring 36 and folding back lateral portion 84 such that the hooks 84a engage the loops 83a on lateral portion 83. Ring 36 is permanently attached to lateral portion 23 of thigh cuff 20 by a plastic tab 37 having a channel through which one side of the ring passes and a rivet 38 which attaches tab 37 to thigh cuff 20.

Figure 4:
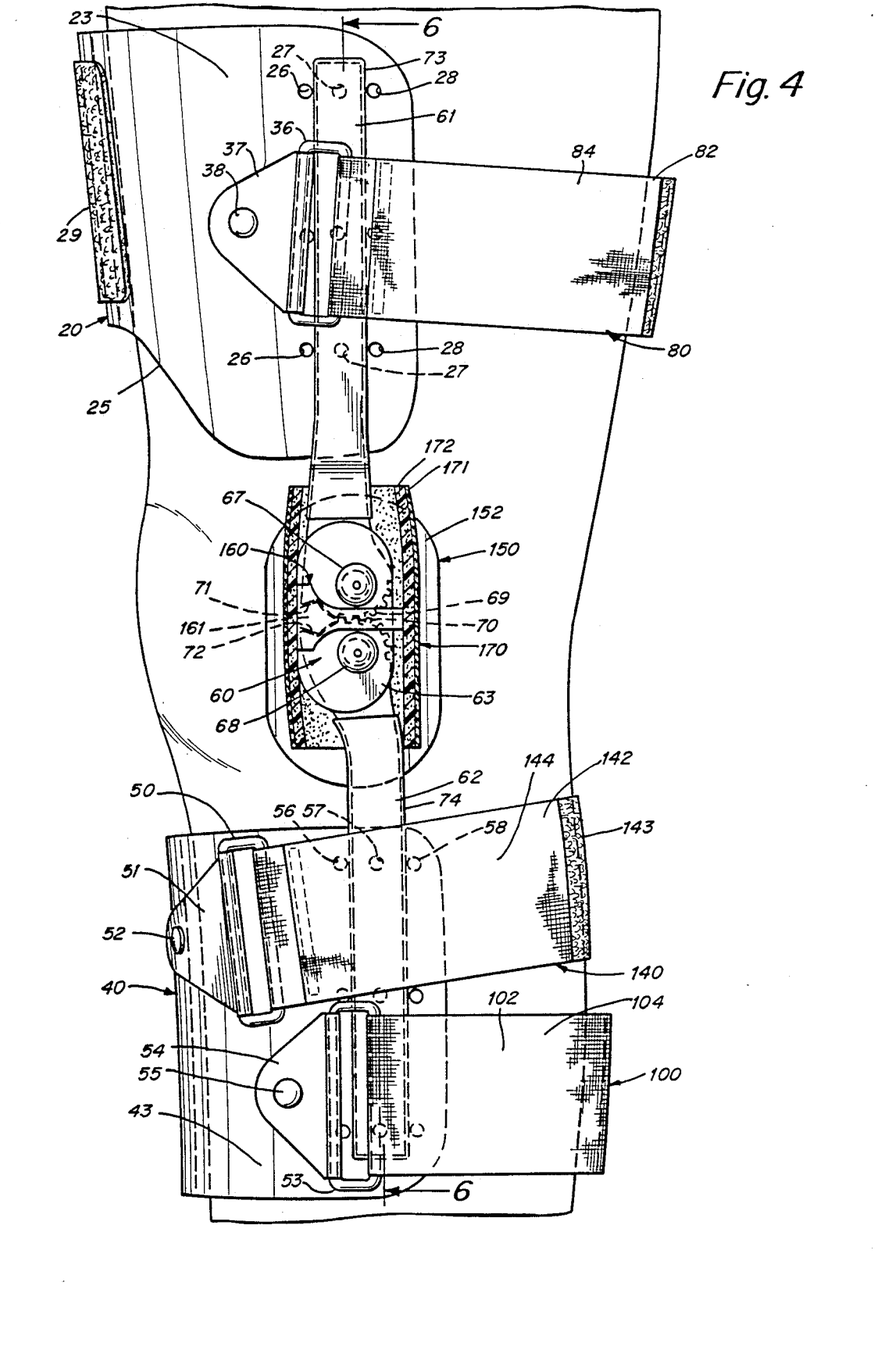
FIG. 4 is a lateral elevation view of the left knee and brace of FIG. 1 (without the outer thigh and calf bands).

Lower shin cuff 40 and lower cuff strap 100 function in much the same manner as the upper thigh cuff 20 and upper cuff strap 80. Thus, shin cuff 40 has a hard outer shell 41 and an inner padded lining 42. Shin cuff 40 includes anterior portion 59, lateral portion 43 and medial portion 44 which conform to the respective portions of the shin and calf. Non-stretchable lower cuff strap 100 includes a medial portion 103 having Velcro loops 103a on its outer surface and padding 108 on its inner surface and a lateral portion 104 having Velcro hooks 104a on its outer surface (FIG. 5). A medial end 101 of strap 100 is permanently attached to medial portion 44 of shin cuff 40 by rivet 106 (FIG. 3). A lateral end 102 of strap 100 is adjustably and releasably attached to lateral portion 43 of shin cuff 40 by passing lateral end 102 through a ring 53 and doubling back onto itself such that the Velcro hooks 104a on lateral portion 104 engage the Velcro loops 103a on medial portion 103 (FIG. 4). A notch or cut-out 45 (FIG. 3) is provided along the upper edge of medial portion 44 to accommodate a non-stretchable posterior strap 140 as described hereinafter.

The non-stretchable upper and lower cuff straps 80, 100 extend approximately horizontally around the back of the leg and prevent the leg from backing out of the brace. Pads 88 and 108 are provided on the inner surfaces of the straps for comfort and to prevent chafing of the leg.

To further stabilize the brace to the leg, a pair of wide, stretchable outer bands 90, 110 are provided in substantially horizontal alignment around the leg over the thigh and shin cuffs, and the cuff straps attached thereto (FIGS. 1-3). Upper band 90 has Velcro hooks at one end (not shown) for releasable attachment to Velcro loops 29 on an anterior portion 39 of thigh cuff 20 (FIG. 2). Thigh band 90 is then wrapped around the leg and secured at the other end by Velcro hooks (not shown) attachable to Velcro loops 96 on the outer surface of the band (FIG. 1). Similarly, lower band 110 is attached at one end with Velcro hooks to Velcro loops 49 on medial portion 44 of shin cuff 40 and is wrapped around the leg and secured at the other end by Velcro hooks to Velcro loops 113 on the outer surface of band 110 (FIGS. 1 and 3).

The thigh and shin cuffs can be made as an off-the-shelf item in different sizes, e.g., small, medium and large. Within each cuff size, differences in girth are accommodated by providing medial-lateral flexibility to the cuff and adjustability to the cuff strap. Furthermore, three sets of vertically aligned apertures are provided on the cuffs for adjustably connecting the lateral hinge thereto, as described hereinafter.

The outer shells 21, 41 of the thigh and shin cuffs are preferably a hard, substantially rigid, molded shell of a polyethylene-polypropylene copolymer, about 3/16" in thickness, which have some medial-lateral flexibility to accommodate legs of varying girth. The shell is impact-resistant and preferably is made of a plastic such as polyethylene or polypropylene, and more preferably a copolymer thereof. Each shell has a ¼" inch foam liner 22, 42 for comfort, for accommodating differences in leg girth, and for suspension (i.e., holding up the brace so it does not slip down on the leg). The lining is a softer, less abrasive material than the shell and preferably is a polyethylene foam sold under the trademark Evazote by Bakelite Xylonite Limited, London, England. The shell is preferably prefabricated from standard molds. The foam liner is applied to the inner surface of the shell by adhesive or by heat bonding.

The upper and lower cuff straps 80, 110 are each 2" wide and are made of two sections of Dacron sewn together end-to-end. The sections have either Velcro hooks or loops on one side thereof. The medial ends of the straps are folded back for reinforcement before attaching the straps with metal rivets to the cuffs. The rings 36, 53 by which the straps are adjustably attached to the cuffs at their lateral ends are 2 ¼" wide metal D-rings. The plastic tabs 37, 54 are double thickness for strength and are attached via metal rivets 38, 55 to the cuffs. The padding sections 88, 108 are about ¼" thick foam rubber pads and are adhesively bonded to the inner surfaces of strap sections 83, 103. The outer bands 90, 110 are about 4" wide and are made of neoprene rubber sold by Rubatex, of Bedford, Va.

Figure 6:
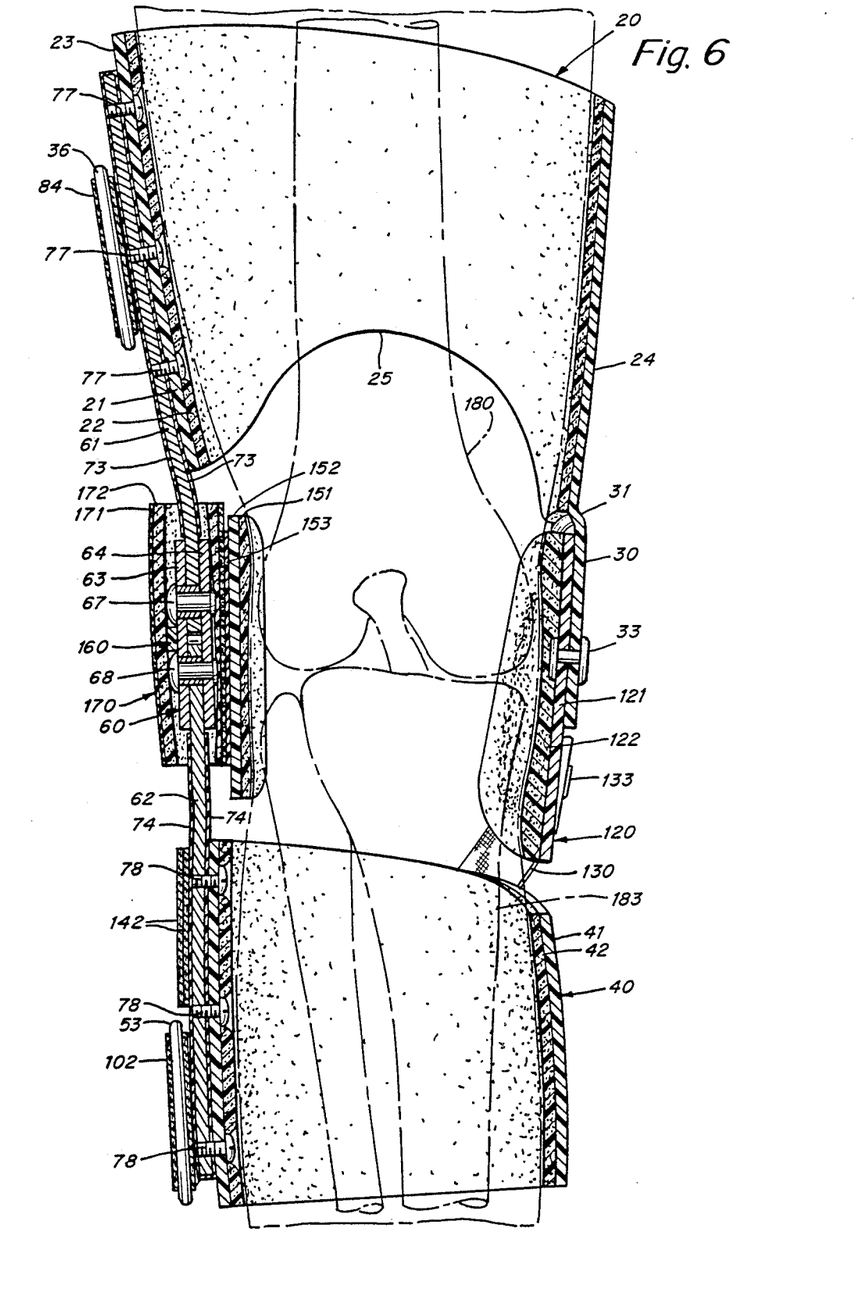
FIG. 6 is a cross sectional view taken along the section lines 6—6 of FIG. 4 showing the leg bones at the knee joint and the anterior cruciate ligament in phantom lines.

As best shown in FIGS. 2, 4 and 6, a polycentric hinge 60 is provided on the lateral side of the knee extending between and connecting lateral portions of the shin and thigh cuffs. The hinge has two pivot points 67, 68 and a pair of shafts or arms 61, 62 extending above and below the pivot points. A pair of spaced-apart outer and inner connecting plates 63, 64 have pairs of aligned apertures through which pins 67, 68 pass to define the pivot points. The upper end of lower shaft 62 is positioned between connecting plates 63, 64 and has an aligned aperture through which lower pivot pin 68 passes. The lower end the lower shaft 62 is attached at three vertically spaced points to the lateral portion 43 of the shin cuff by threaded screws 78 which pass through aligned apertures in the shaft and cuff (FIG. 6). Similarly, the lower end of the upper shaft 61 is positioned between connecting plates 63, 64 and has an aligned aperture through which upper pivot pin 67 passes. The upper end of upper shaft 61 is attached to the lateral portion 23 of thigh cuff 20 by three threaded screws 77 (FIG. 6). The shafts 61, 62 are preferably 8" in length to provide substantial leverage and are made of a high-strength, light-weight alloy. The shafts 61, 62 pivot around their respective pivot points 67, 68 and have intermeshing gear teeth 69, 70 at their mating ends so as to cause simultaneous pivotal action of both shafts about their pivotal connections with the plates. The shafts maintain the vertical alignment of the femur 180 and tibia 183 (FIGS. 6-7), prevent excessive rotation of the tibia with respect to the femur, and permit substantially natural flexion and extension of the knee. Preferably, a non-abrasive polymeric coating 73, 74 is provided on the upper and lower shafts to prevent injury. The polycentric hinge is fully described in U.S. Pat. No. 4,633,867 to Kausek et al. which is hereby incorporated by reference. Preferably, an extension stop 160 (FIGS. 2 and 4) is provided for limiting the forward pivotal rotation of the shafts, as described in U.S. Pat. No. 4,732,143 to Kausek et al., which is hereby incorporated by reference. Flanges 71, 72 on the ends of shafts 61, 62 adjacent the gear teeth engage an extension block 161 for preventing the knee from pivoting forwardly beyond the maximum desired articulation, i.e., preventing hyperextension.

The central portion of hinge 60 is encased by a padded tubular sleeve 170 which prevents chafing against the knee and injury to articles which it may contact. Sleeve 170 also allows attachment of a lateral plate as described hereinafter. The sleeve may be made of rubber or neoprene. The outer surface of the sleeve has a loop material which acts as Velcro loops for the releasable attachment of the lateral plate.

The lateral plate 150 is designed to engage the lateral side of the knee so as to anchor the brace on the knee and control ligament instability. Plate 150 includes a hard and substantially rigid outer shell 52 and an inner soft pad 51 of a non-abrasive, resilient material which is shaped to conform to the tibial and femoral condyles at the lateral side of the knee. Velcro hooks 53 are attached to the back of the shell for releasable attachment to the hinge cover 170. Alternatively, the lateral plate 150 may be affixed by adhesive or rivets to the inner hinge plate 64 and the sleeve 170 applied over the hinge and lateral plate.

At the medial side of the knee, as shown in FIGS. 2, 3, 5 and 6, there is provided a medial articulation plate 120. Plate 120 is designed to engage the tibial and femoral condyles at the medial side of the knee so as to stabilize the brace and provide a medial point of articulation. Medial plate 120 has a hard, substantially rigid outer shell 121 and an inner lining 122 of a non-abrasive, resilient material which is shaped to conform to the medial knee joint. The plate 120 has three points of attachment, defined by an upper pivot pin 33 and two lower rivets 133 and 146. A medial flange 30 extends downwardly from medial portion 24 of thigh cuff 20 and over the outer surface of plate 120 via outwardly curved shoulder 31 (FIG. 2). A rigid plastic pivot pin 33 extends through aligned apertures in medial flange 30 and medial plate 120 for pivotally connecting the same. The vertical position of the medial pivot pin 33 is between and preferably at about the mid-point between the pivot pins 67, 68 of the lateral hinge. The outer shells 52, 121 of the lateral and medial condylar plates are made of the same material and thickness as the cuffs 20, 40. The inner pads 51, 122 are preferably about ⅜" thick and made of a polymer foam such as foam rubber. Preferably, medial plate 120 is an elongated oval about 4 ¼" in length and 3" in width and the shell and padding are slightly concave (inwardly).

A stretchable anterior strap 130 is non-pivotally and permanently attached at its upper end 131 to a lower, anterior attachment point on medial plate 120 by metal rivet 133. Strap 130 then extends anteriorly and downwardly at an angle of about 45° and is non-pivotally attached at its lower end 132 to the anterior portion 59 of shin cuff 40 by metal rivet 134. Anterior strap 130 allows limited vertical separation of the medial plate 120 and shin cuff 40 during knee flexion to prevent the shin cuff from riding up on the leg. Furthermore, in conjunction with a posterior strap 140 described hereinafter, it prevents the lower end of medial plate 120 from pivoting forwardly and thus restrains anterior movement of the tibia with respect to the femur. As shown, front medial strap 130 is about 3.25" in length and is made of a cotton-covered elastic. Fabric reinforcements 135, 136 made of nylon are provided at each end of the strap for more secure attachment to the lower cuff and medial plate.

A non-stretchable posterior strap 140 is provided between medial plate 120 and shin cuff 40 to restrain forward movement of the lower end of medial plate 120 as it pivots about pin 33 during flexion of the knee. Medial end 141 of strap 140 is permanently and non-pivotally attached by metal rivet 46 to a lower, posterior attachment point on medial plate 120. Strap 140 includes medial portion 143 having Velcro loops on its outer surface and lateral portion 144 having Velcro hooks on its outer surface (FIG. 5). Strap 140 extends behind the back of the leg and is adjustably and releasably secured to the lateral portion of the shin cuff by metal D-ring 50 which is attached by plastic tab 51 and metal rivet 52 to shin cuff 40. The lateral end 142 of strap 140 is passed through the D-ring and pulled back on itself for attaching Velcro hooks on section 144 to Velcro loops on section 143. Strap 140 is preferably of the same construction as the cuff straps 80, 100.

Figure 7:
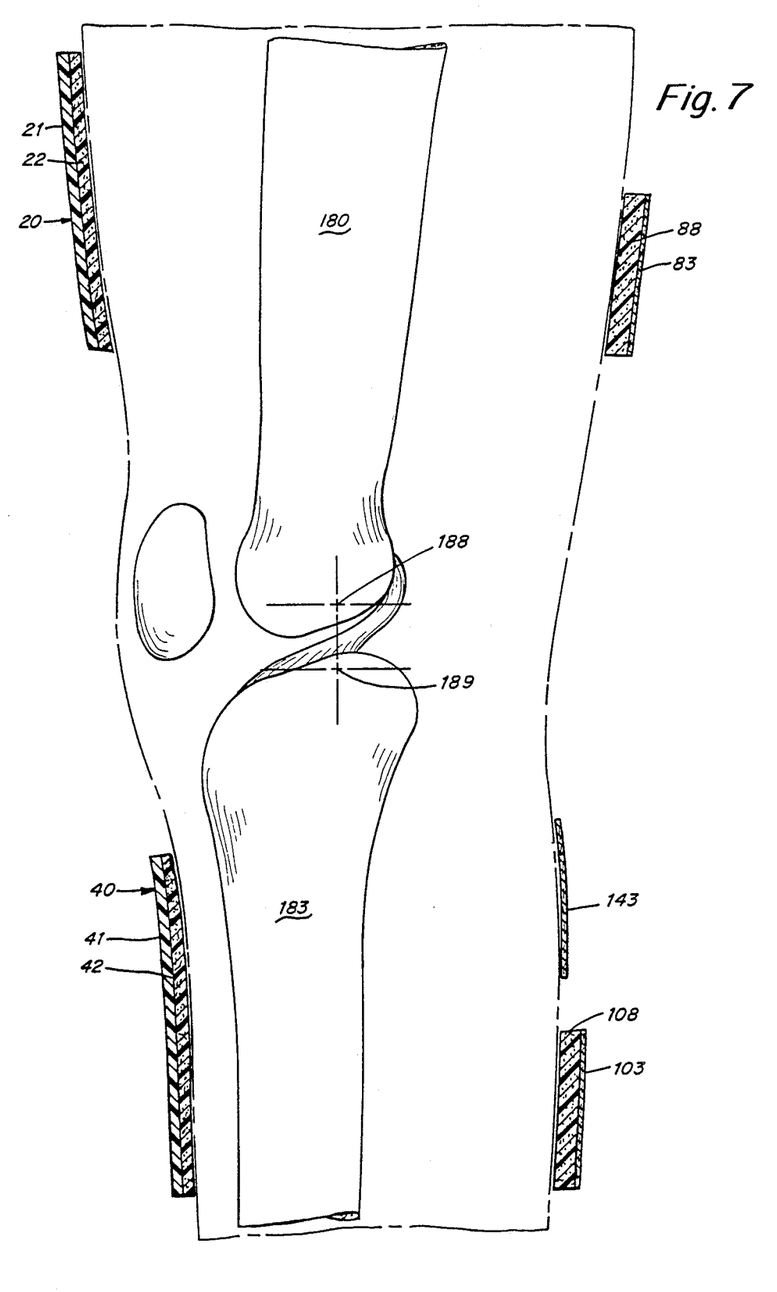
FIG. 7 is a schematic view of the lateral side of the left knee showing the anterior cruciate ligament and the two pivot points of the polycentric hinge.
Figure 8:
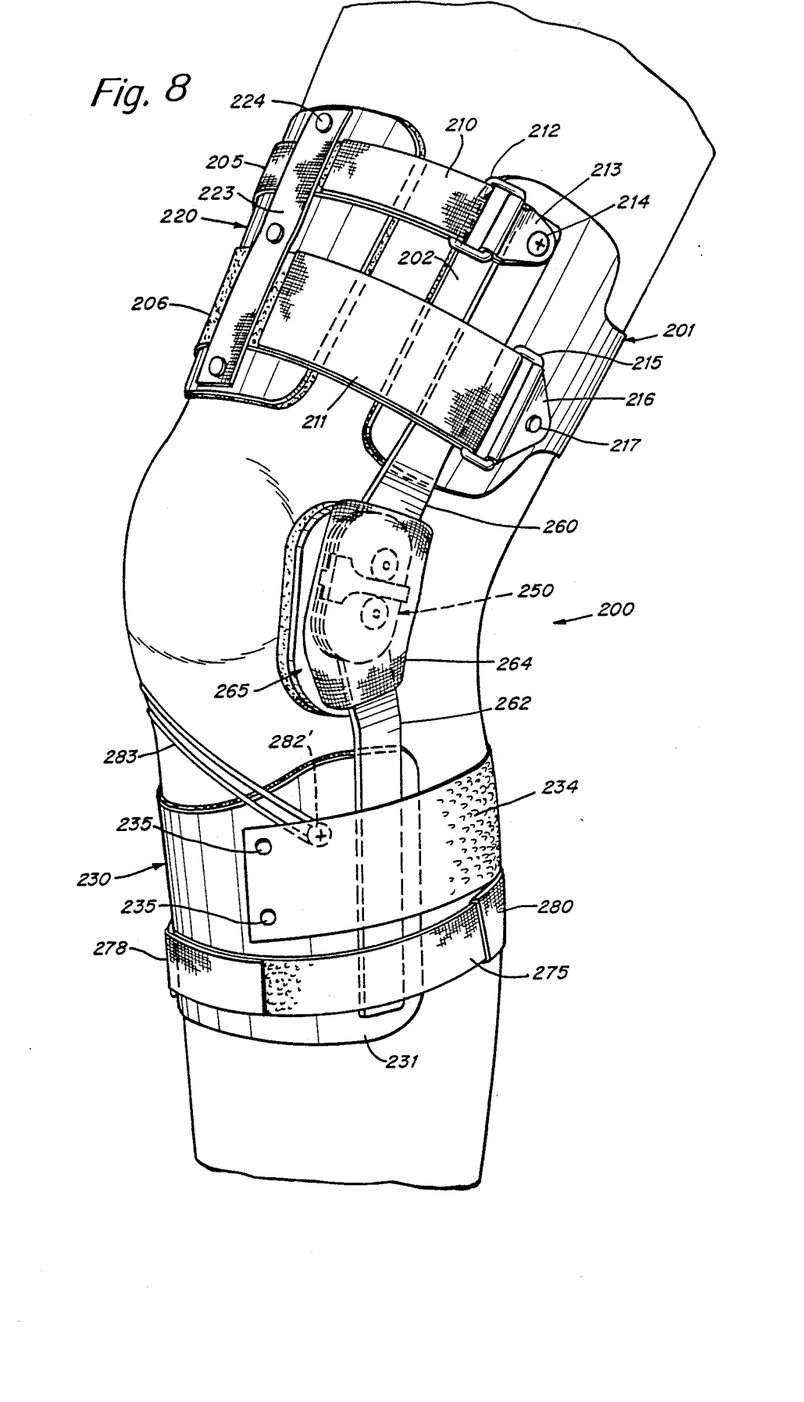
FIG. 8 is a lateral perspective view of a second embodiment of the knee brace of this invention.
Figure 9:
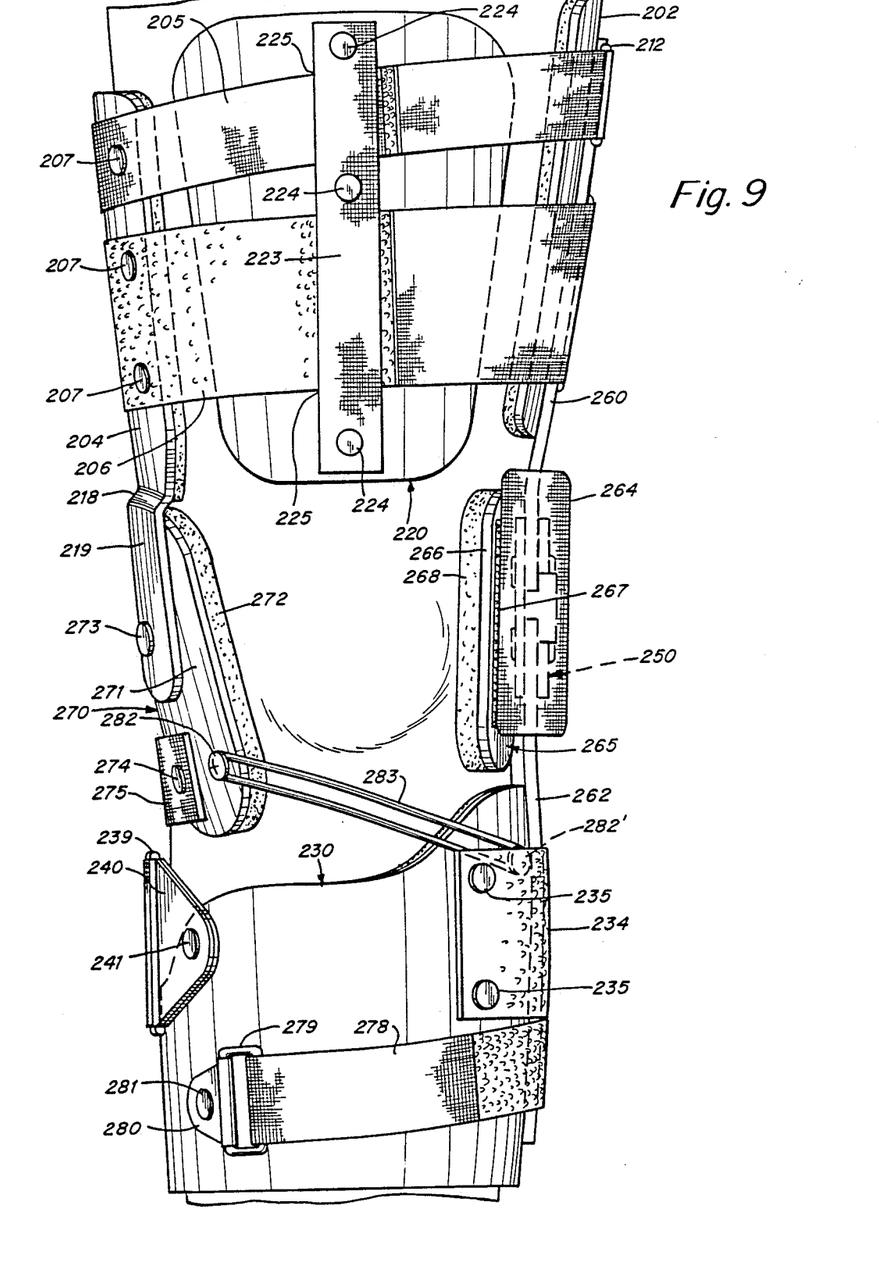
FIG. 9 is a front elevation view of the knee brace of FIG. 8.
Figure 10:
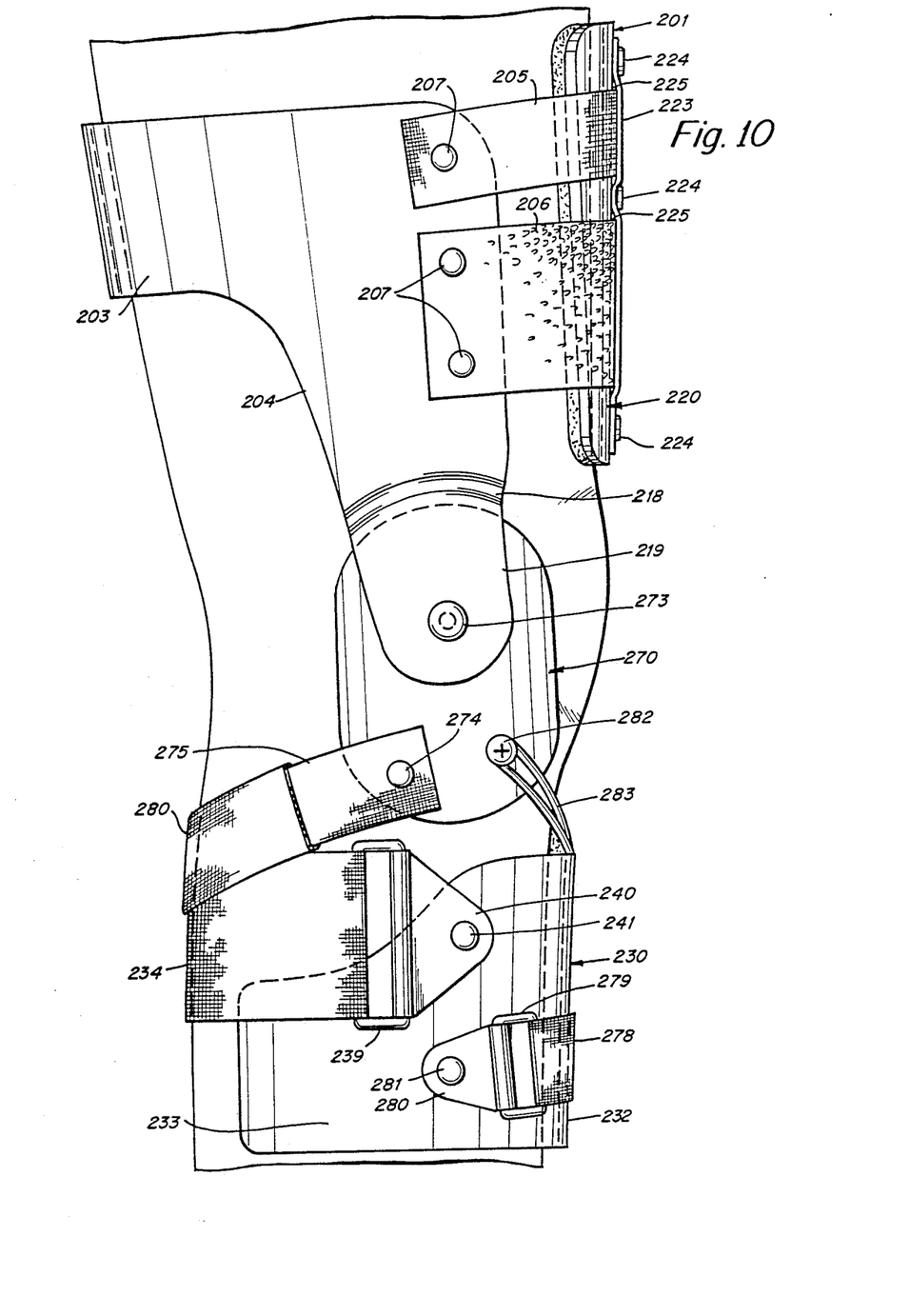
FIG. 10 is a medial elevation view of the knee brace of FIG. 8.
Figure 11:
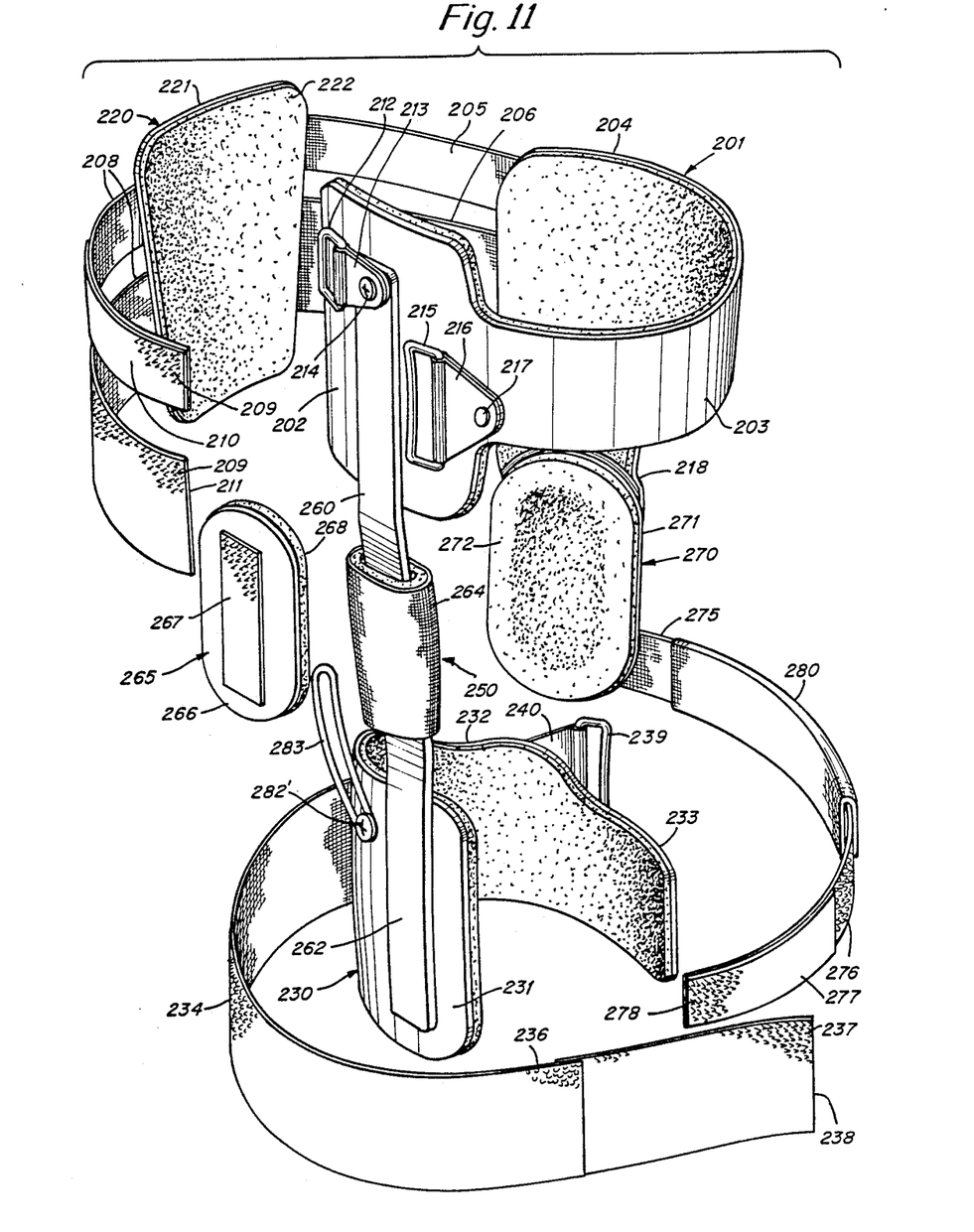
FIG. 11 is an exploded rear perspective view showing the various components of the knee brace of FIG. 8.

The anterior and posterior straps 130, 140 unify the thigh and shin cuffs at the medial side of the brace without the use of a second polycentric hinge. They also affix the medial plate to the knee to provide a medial point of articulation. The lateral polycentric hinge 60 approximates the two pivot points of the natural knee, as shown in FIG. 7 at 188 and 189.

A second embodiment of the invention is shown in FIGS. 8-11. In the second embodiment the upper cuff engages the back of the thigh, as compared to the first embodiment wherein the upper cuff engages the front of the thigh. The second embodiment functions in substantially the same manner as the first embodiment and thus will be described with less detail.

The knee brace 200 of the second embodiment includes an upper cuff 201 having a lateral portion 202, posterior portion 203, and medial portion 204. A pair of non-stretchable upper cuff straps 205, 206 are attached by rivets 207 to medial portion 204 and are wrapped in parallel alignment around the front of the thigh. Upper cuff straps 205, 206 have Velcro loops 208 on their outer surfaces and Velcro hooks 209 on the outer surfaces of distal end portions 210 and 211. Distal end 210 of strap 205 is releasably and adjustably secured by passing through ring 212 attached by tab 213 and rivet 214 to an upper hinge arm 260 attached to lateral portion 202 of upper cuff 201. Distal end 210 is then folded back onto strap 205 such that hooks 209 engage loops 208. In a similar manner, distal end 211 of strap 206 passes through ring 215 which is attached by tab 216 and rivet 217 to lateral portion 202 of cuff 201.

A thigh plate 220 having a hard outer shell 221 and soft lining 222 is positionable on the front of the thigh and shaped to conform thereto. A vertically disposed metal strip 223 is attached by metal rivets 224 at three vertically spaced points to the outer shell 221 of thigh plate 220. A pair of channels 225 are defined between strip 223 and plate 220 between adjacent pairs of rivets 224 through which upper cuff straps 205, 206 pass for positioning thigh plate 220 on the front of the thigh. Channels 225 may be somewhat wider than straps 205, 206 to allow some vertical adjustability of thigh plate 220 on the thigh.

Knee brace 200 further includes a lower cuff 230 having a lateral portion 231, anterior portion 232, and medial portion 233. A non-stretchable lower cuff strap 234 is attached at one end by a pair of rivets 235 to anterior portion 232 of lower cuff 230. Strap 235 has Velcro loops 236 on its outer surface and a distal end portion 238 having Velcro hooks 237 on its outer surface. Strap 234 is wrapped around the back of the leg and is adjustably and releasably connected by passing distal end 238 through ring 239 which is attached by tab 240 and rivet 241 to medial portion 233 of lower cuff 230. Distal end 238 is then folded back such that Velcro hooks 237 engage Velcro loops 236.

A polycentric hinge 250 is disposed at the lateral side of the knee. Hinge 250 is identical to hinge 60 of the first embodiment and will therefore not be described in detail. Hinge 250 includes an upper arm 260 attached by three vertically aligned rivets 261 to lateral portion 202 of upper cuff 201 and has a lower arm 262 which is attached by three vertically aligned rivets 263 to lateral portion 231 of lower cuff 230. Hinge 250 has a tubular sleeve 264 covering the central hinge portion. Sleeve 264 has Velcro loops on its outer surface for attachment to Velcro hooks 267 on lateral plate 265. Plate 265 has an outer shell 266 and a softer lining 268 shaped to conform to the lateral side of the knee.

Knee brace 200 further includes a medial plate 270 having an outer shell 271 and a softer lining 272 shaped to conform to the medial side of the knee. A lower flange 219 extending from medial portion 204 of upper cuff 200 is offset outwardly of medial portion 204 by shoulder 218 so that flange 219 lies over the outer surface of medial plate 270. Similar to the medial plate of the first embodiment, an upper pivot point 273 connects the flange 219 and plate 270 and a lower posterior rivet 274 connects one end of a non-stretchable posterior strap 275 to medial plate 270. Strap 275 is wrapped around the back of the calf and is connected at its opposite end to lower cuff 230. Strap 275 has loops 276 on its outer surface and Velcro hooks 277 on a distal end portion 278. Distal end 278 passes through ring 279 which is attached by tab 280 and rivet 281 to anterior portion 232 of lower cuff 230. End 278 is folded back so that hooks 277 engage loop 276. A pad 280 is provided on a central portion of shaft 275 to prevent chaffing against the back of the leg.

An anterior lower attachment point between medial plate 270 and lower cuff 230 is defined by post or screw 281 on the outer shell 271 of plate 270. A second post or screw 282 is provided on the anterior portion 232 of lower cuff 230. A stretchable band or strap 283 forms a closed loop with opposite ends disposed around posts 281 and 282. Strap 283 functions in a manner similar to strap 130 of the first embodiment.

Although certain preferred embodiments of the invention have hereinbefore been described, it will be appreciated that variations of the invention will be perceived by those skilled in the art, which variations are nevertheless within the scope of the invention as defined by the claims appended hereto.

What is claimed is:

1. A knee brace comprising:
   an upper cuff positionable above the knee and a lower cuff positionable below the knee;
   means for attaching each of the upper and lower cuffs to the leg;
   a lateral hinge for preventing medial-lateral displacement of the upper and lower cuffs, the hinge having upper and lower hinge arms and at least one pivot point positionable adjacent the lateral side of the knee;
   each of the upper and lower cuffs being shaped to conform to the leg and having medial and lateral portions;
   means for connecting the upper hinge arm to the lateral portion of the upper cuff and the lower hinge arm to the lateral portion of the lower cuff;
   a medial plate to stabilize the brace positionable at the medial side of the knee and having an inner surface for engaging the medial side of the knee; and
   means for connecting the medial plate to each of the upper and lower cuffs, said connecting means including a pivotal connecting means between the medial plate and medial portion of the upper cuff to provide a medial point of articulation from which the plate pivots in a substantially anterior-posterior direction, and a means connecting the medial plate and lower cuff for restraining anterior movement of the tibia with respect to the femur including an anterior strap extending from the medial plate to the lower cuff and a posterior strap extending from the medial plate to the lower cuff;
   wherein the upper and lower cuffs provide anterior-posterior stability to the knee joint and the lateral hinge and medial plate provide medial-lateral stability.

2. The knee brace of claim 1, wherein the upper cuff has a lower flange positionable adjacent the outer surface of the medial plate and the medial plate is pivotally connected to the flange.

3. The knee brace of claim 2, wherein the posterior strap is substantially non-stretchable and positionable around the back of the leg.

4. The knee brace of claim 3, wherein the anterior strap is stretchable and disposed at the front of the leg.

5. The knee brace of claim 4, wherein the upper cuff extends around the medial, anterior and lateral sides of the leg and the means for attaching the upper cuff to the leg is disposed around the back of the leg.

6. The knee brace of claim 4, wherein the upper cuff extends around the medial, posterior and lateral sides of the leg and the means for attaching the upper cuff to the leg is disposed around the front of the leg.

7. The knee brace of claim 6, further comprising a substantially rigid thigh plate disposed at the front of the leg and attached to the means for attaching the upper cuff to the leg.

8. The knee brace of claim 1, further including a lateral plate positioned on the inner side of the lateral hinge for engaging the lateral side of the knee.

9. The knee brace of claim 2, wherein the lateral hinge has two pivot points.

10. The knee brace of claim 9, wherein
the pivotal connection between the medial plate and flange is between the two lateral pivot points.

11. The knee brace of claim 1, wherein
the upper and lower cuffs are flexible in the medial-lateral direction and the means for attaching the cuffs to the leg are adjustable so that the brace can accommodate different leg girths.

12. The knee brace of claim 11, wherein
the lateral portions of the upper and lower cuffs have a plurality of attachment means in spaced anterior-posterior relationship for adjustable attachment of the lateral hinge to the upper and lower cuffs.

13. The knee brace of claim 12, wherein
the plurality of attachment means includes sets of vertically-aligned apertures.

14. The knee brace of claim 1, further comprising
a pair of upper and lower stretchable bands positionable over the brace and around the leg, the upper band being positionable above the knee around the upper cuff and the lower band being positionable below the knee around the lower cuff.

15. The knee brace of claim 1, wherein
the means for attaching the cuffs to the leg comprise substantially non-stretchable cuff straps with adjustable fastening means.

16. The knee brace of claim 15, wherein
the cuff straps have padding on their interior surfaces adjacent the leg to prevent chafing.

17. The knee brace of claim 1, wherein
the lower cuff extends around the medial, anterior and lateral sides of the leg and the means for attaching the lower cuff to the leg is disposed around the back of the leg.

18. A knee brace comprising:
an upper cuff positionable above the knee, the upper cuff including medial and lateral portions;
an upper cuff strap for securing the upper cuff to the leg;
a lower cuff positionable below the knee, the lower cuff including medial and lateral portions;
a lower cuff strap for securing the lower cuff to the leg,
a hinge for preventing medial-lateral displacement of the upper and lower cuffs, the hinge being positionable at the lateral side of the knee for connecting the lateral portion of the upper cuff and the lateral portion of the lower cuff and providing at least one pivot point therebetween;
a medial plate to stabilize the brace positionable at the medial side of the knee and having an inner surface for engaging the medial side of the knee;
pivotal connecting means at an upper point of attachment between the medial plate and the medial portion of the upper cuff to provide a medial articulation point from which the plate pivots in a substantially anterior-posterior direction;
non-pivotal connecting means at at least one lower point of attachment on the medial plate;
a stretchable anterior strap extending from the at least one lower point of attachment and laterally adjacent the front of the leg to the lower cuff for connecting the medial plate to the lower cuff;
a non-stretchable posterior strap extending from the at least one lower point of attachment and laterally adjacent the back of the leg to the lower cuff for connecting the medial plate to the lower cuff, the anterior and posterior straps restraining anterior movement of the tibia with respect to the femur;
wherein the upper and lower cuffs provide anterior-posterior stability to the knee joint and the lateral hinge and medial plate provide medial-lateral stability.

19. The knee brace of claim 15, further comprising
a lateral plate positionable at the lateral side of the knee and having an inner surface for engaging the lateral side of the knee.

20. The knee brace of claim 15, wherein
the medial portion of the upper cuff has a flange extending downwardly adjacent the medial side of the knee to which the medial plate is pivotally attached at the upper point of attachment.

21. The knee brace of claim 20, wherein
the flange is connected to the upper cuff by an outwardly-curved shoulder.

22. A knee brace comprising:
an upper cuff positionable above the knee and means for securing the upper cuff to the leg;
a lower cuff positionable below the knee and means for securing the lower cuff to the leg;
a hinge positionable at the lateral side of the knee for preventing medial-lateral displacement of the upper and lower cuffs, the hinge including upper and lower hinge arms connected to the upper and lower cuffs respectively and means for providing at least one pivot point between the arms adjacent the side of the knee;
a medial plate to stabilize the brace positionable at the medial side of the knee and having an inner surface for engaging the medial side of the knee, means for pivotally connecting the medial plate and the upper cuff to provide a medial point of articulation adjacent the knee from which the plate pivots in a substantially anterior-posterior direction, and means for connecting the medial plate and the lower cuff to restrain anterior movement of the tibia with respect to the femur, the means for connecting the medial plate and the lower cuff including an anterior strap extending from the medial plate tot he lower cuff and a posterior strap extending from the medial plate to the lower cuff;
wherein the knee brace provides both anterior-posterior and medial-lateral stability.

23. The knee brace of claim 22, wherein
the anterior strap extends laterally from the medial plate and is positioned adjacent the front of the leg; and
the posterior strap extends laterally from the medial plate and is positioned adjacent the back of the leg.

24. The knee brace of claim 23, wherein
the anterior strap is stretchable and the posterior strap is non-stretchable.

25. The knee brace of claim 22, wherein
the upper cuff and lower cuff each include lateral portions and the hinge arms are connected to the lateral portions of the upper and lower cuffs respectively.

26. The knee brace of claim 22, further including
a lateral plate positionable on the inner side of the lateral hinge for engaging the lateral side of the knee.

* * * * *